US009096477B2

(12) United States Patent
Panicheva et al.

(10) Patent No.: US 9,096,477 B2
(45) Date of Patent: Aug. 4, 2015

(54) ELECTROCHEMICALLY TREATED NUTRIENT SOLUTIONS

(71) Applicant: Puricore, Inc., Malvern, PA (US)

(72) Inventors: Svetlana Panicheva, Malvern, PA (US); Mark N. Sampson, Malvern, PA (US)

(73) Assignee: PuriCore, Inc., Malvern, PA (US)

( * ) Notice: Subject to any disclaimer, the term of this patent is extended or adjusted under 35 U.S.C. 154(b) by 0 days.

(21) Appl. No.: 13/735,269

(22) Filed: Jan. 7, 2013

(65) Prior Publication Data

US 2013/0190173 A1 Jul. 25, 2013

Related U.S. Application Data

(60) Provisional application No. 61/583,927, filed on Jan. 6, 2012.

(51) Int. Cl.
| G01F 1/64 | (2006.01) |
| G01N 17/00 | (2006.01) |
| G01N 27/26 | (2006.01) |
| C05G 3/02 | (2006.01) |
| C05D 9/00 | (2006.01) |
| A01N 59/00 | (2006.01) |

(52) U.S. Cl.
CPC *C05G 3/02* (2013.01); *A01N 59/00* (2013.01); *C05D 9/00* (2013.01)

(58) Field of Classification Search
CPC ............ C05G 3/02; C05G 3/0076; C05D 9/00
USPC ................ 205/775, 778.5, 779.5, 781.5, 782, 205/785.5, 787.5
See application file for complete search history.

(56) References Cited

U.S. PATENT DOCUMENTS

| 3,287,104 | A | 11/1966 | Biggs |
| 4,278,715 | A | 7/1981 | Romero-Sierra et al. |
| 5,080,707 | A | 1/1992 | Ide et al. |
| 5,171,351 | A | 12/1992 | Yamamoto et al. |
| 5,213,604 | A | 5/1993 | Saito et al. |
| 5,284,818 | A | 2/1994 | Shafer et al. |
| 5,366,954 | A | 11/1994 | Bestwick et al. |
| 5,421,121 | A | 6/1995 | Bestwick et al. |
| 5,500,403 | A | 3/1996 | Shafer et al. |
| 5,536,155 | A | 7/1996 | Futaki et al. |
| 5,580,840 | A | 12/1996 | Harms et al. |
| 5,599,571 | A | 2/1997 | Estrada |
| 5,679,617 | A | 10/1997 | Hanafusa et al. |
| 5,817,600 | A | 10/1998 | Carstairs et al. |
| 5,961,886 | A | 10/1999 | Hashimoto et al. |
| 6,264,839 | B1* | 7/2001 | Mohr et al. .................... 210/687 |
| 6,699,707 | B1 | 3/2004 | Hince |
| 6,927,192 | B2 | 8/2005 | Martinelli et al. |
| 7,144,841 | B2 | 12/2006 | Pius |
| 7,199,082 | B1 | 4/2007 | Chapman et al. |
| 7,273,831 | B1 | 9/2007 | Fleskes et al. |
| 7,276,255 | B2 | 10/2007 | Selkon |
| 2002/0182262 | A1 | 12/2002 | Selkon |
| 2005/0233900 | A1* | 10/2005 | Smith et al. .................... 502/407 |
| 2007/0017820 | A1 | 1/2007 | Anderson et al. |
| 2007/0108064 | A1 | 5/2007 | Buckley et al. |
| 2007/0217946 | A1* | 9/2007 | Smith et al. ....................... 422/5 |
| 2007/0231247 | A1 | 10/2007 | Bromberg et al. |
| 2008/0014306 | A1 | 1/2008 | Castro |
| 2008/0047844 | A1* | 2/2008 | Miyashita ..................... 205/743 |
| 2008/0160612 | A1 | 7/2008 | Selkon |
| 2009/0008268 | A1 | 1/2009 | Salathe et al. |
| 2009/0092685 | A1 | 4/2009 | Selkon |
| 2009/0169646 | A1 | 7/2009 | Bosch et al. |
| 2009/0181107 | A1 | 7/2009 | Buckley et al. |
| 2010/0030132 | A1 | 2/2010 | Niezgoda et al. |
| 2010/0285151 | A1 | 11/2010 | Goldan et al. |
| 2011/0028319 | A1* | 2/2011 | Panicheva et al. ............ 504/114 |
| 2011/0294830 | A1 | 12/2011 | Iwata et al. |
| 2012/0024028 | A1 | 2/2012 | Panicheva et al. |
| 2012/0237616 | A1 | 9/2012 | Panicheva et al. |
| 2013/0261534 | A1 | 10/2013 | Niezgoda et al. |

FOREIGN PATENT DOCUMENTS

| DE | 10 2006 043267 | 3/2008 |
| KR | 10-2007-008118 | 8/2007 |
| WO | WO 03/075638 | 9/2003 |
| WO | WO 2004/027116 | 4/2004 |

OTHER PUBLICATIONS

Definition of hectorite clay (obtained via http://en.wikipedia.org/wiki/Hectorite).*
Definition of montmorillonite clay (obtained via http://en.wikipedia.org/wiki/Montmorillonite).*
The article: Dichlorine Monoxide (obtained via www.en.wikipedia.org on Nov. 20, 2014).*
International Search Report and Written Opinion for International Application No. PCT/US2013/020209, mailed on May 8, 2013, 8 pages.
International Search Report and Written Opinion for International Application No. PCT/US2011/043590, mailed on Nov. 30, 2011, 8 pages.
International Search Report and Written Opinion for International Application No. PCT/US2010/043495, mailed Dec. 22, 2011, 11 pages.
Al-Haq, M. I. et al., "Applications of electrolyzed water in agriculture & food industries," Food Science Technologies Research, 11(2):135-150 (2005).

(Continued)

Primary Examiner — Mina Haghighatian
Assistant Examiner — Helen Chui
(74) Attorney, Agent, or Firm — Morgan, Lewis & Bockius LLP

(57) ABSTRACT

The invention relates to nutrient compositions for agricultural applications, and methods for plant or crop growth and care. The nutrient composition comprises a potassium-based nutrient solution enriched by electrochemical treatment. In various embodiments, the potassium-based nutrient composition comprises hypochlorous acid. The present invention involves the use of the nutrient compositions or solutions, among other things, in pre-harvest and post-harvest treatments and in environmental and soil disinfection.

10 Claims, 6 Drawing Sheets

(56) References Cited

OTHER PUBLICATIONS

Haq, A. U. et al, "Effect of nitrogen, phosphorus and potassium on vegetative and reproductive growth of rose (*Rosa centifolia*)," International Journal of Agriculture & Biology, 1(1/2):27-29 (1999).

ATS ECA Water Brochure, ATS unique technologies BV (6 pages); www.agro-technical.com/downloads/eng/pdf_eng8.pdf.

Buck, J. W. et al., "In vitro fungicidal activity of acidic electrolyzed oxidizing water," Plant Disease, 86(3):278-281 (2002).

Clark, J. et al, "Efficacy of super-oxidized water fogging in environmental decontamination," Journal of Hospital Infection, 64:386-390 (2006).

Gast, K. L. B., "Postharvest Handling of Fresh Cut Flowers and Plant Material," http://lwww.ksre.ksu.edu/library/hort2/mf2261.pdf, Kansas State University Agricultural Experiment Station and Cooperative Extension Service (1997), pp. 1-12.

Hur, J-S et al., "Inhibitory effects of super reductive water on plant pathogenic fungi," Plant Pathology Journal 18(5):284-287 (2002).

Kates, S. G. et al., "Indigenous multiresistant bacteria from flowers in hospital and nonhospital environments," American Journal of Infection Control, 19(3):156-161 (1991).

Larson, R. A. (ed.), Introduction to Floriculture Second Edition, Academic Press, Inc. San Diego, CA (1980, 1992) pp. 11, 13, 51, 79, 88 and 91.

Loshon, C. A. et al., "Analysis of the killing of spores of *Bacillus subtilis* by a new disinfectant, Sterilox®," Journal of Applied Microbiology, 91(6):1051-1058 (2001).

Martin, M. V. et al., "An investigation of the efficacy of super-oxidised (Optident/Sterilox) water for the disinfection of dental unit water lines," British Dental Journal, 198(6):353-354 (2005).

Melly, E. et al., "Analysis of the properties of spores of *Bacillus subtilis* prepared at different temperatures," Journal of Applied Microbiology, 92(6):1105-1115 (2002).

Middleton, A. M. et al, "Comparison of a solution of super-oxidized water (Sterilox®) with glutaraldehyde for the disinfection of bronchoscopes, contaminated in vitro with *Mycobacterium tuberculosis* and *Mycobacterium avium-intracellulare* in sputum," Journal of Hospital Infection, 45(4):278-282 (2000).

Nakagawara, S. et al., "Spectroscopic characterization and the pH dependence of bactericidal activity of the aqueous chlorine solution," Analytical Sciences, 14(1):691-698 (1998).

Park, G. W. et al, "Evaluation of Liquid- and Fog-Based Application of Sterilox Hypochlorous Acid Solution for Surface Inactivation of Human Norovirus," Applied and Environmental Microbiology, 73(14):4463-4468 (2007).

Pineau, L., "Etude 99-E-229 Sterilox/Lancer Preliminary Report" (1999) pp. 1-6.

Selkon, J. B. et al., "Evaluation of the antimicrobial activity of a new super-oxidized water, Sterilox®, for the disinfection of endoscopes," Journal of Hospital Infection, 41:59-69 (1999).

Selkon, J. B., "Development of a New Antiseptic for Treating Wound Infection," The Oxford European Wound Healing Course Handbook. Wound Healing Institute, Oxford, England, pp. 159-164 (2002).

Shetty, N. et al., "Evaluation of microbicidal activity of a new disinfectant: Sterilox® 2500 against *Clostridium difficile* spores, *Helicobacter pylori*, vancomycin resistant *Enterococcus* species, *Candida albicans* and several *Mycobacterium* species," Journal of Hospital Infection, 41(2):101-105 (1999).

Silberbush, M. et al., "Nitrate and potassium uptake by greenhouse roses (*Rosa hybrida*) along successive flower-cut cycles: a model and its calibration," Scientia Horticulturae, 101:127-141 (2004).

Starck, J. R. et al., "Effect of Fertiliser Nitrogen and Potassium Upon Yield and Quality of Carnations Grown in Peat and Sawdust," Abstract ISHS Acta Horticulturae 294: II Symposium on Horticultural Substrates and their Analysis, XXIII IHC http://www.actahort.org/members/showpdf?booknrarnr=294_31 as downloaded Jul. 23, 2009, 2 pages.

Tapper, R. C. et al., "Atomic force microscopy study of the biocidal effect of super-oxidised water, Sterilox," Biofilm, vol. 3, Paper 4 (BF98004) (Jul. 10, 1998) Online Journal—URL: http://www.bdt.org.br/bioline/bf (printed from http://www.bioline.org.br/request?bf98004 Aug. 1, 2002) 16 pages (8 text, 8 photographs).

Walker, J. T. et al., "Microbiological Evaluation of a Range of Disinfectant Products to Control Mixed-Species Biofilm Contamination in a Laboratory Model of a Dental Unit Water System," Applied and Environmental Microbiology, 69(6):3327-3332 (2003).

Zinkevich, V. et al., "The effect of super-oxidized water on *Escherichia coli*," Journal of Hospital Infection, 46:153-156 (2000).

Excerpt of Oxford Dictionary of Chemistry, Potassium Chlorate, p. 457 (2004).

Kemme, R., "Preserving Cut Flowers," University of Illinois Extension Master Gardener News Column (2007), 3 pages.

Harada, K., "Behavior of Hydrogen Peroxide in Electrolyzed Anode Water," Biosci. Biotechnol. Biochem, 66(9):1783-1791 (2002).

Reid, M. S., "Cut Flowers and Greens," Department of Environmental Horticulture, University of California, Davis, CA (2001).

\* cited by examiner

ELECTROCHEMICALLY TREATED NUTRIENT SOLUTIONS

PRIORITY

This application claims priority to and the benefit of U.S. Provisional Application No. 61/583,927, filed Jan. 6, 2012, which is hereby incorporated by reference in its entirety.

RELATED APPLICATIONS

The subject matter of this application is related to the subject matter disclosed in U.S. application Ser. No. 13/180,296, filed Jul. 11, 2011, which is hereby incorporated by reference in its entirety.

BACKGROUND

Nutrient compositions with preservative properties are of great need for a variety of agricultural applications, such as, for example, hydroponics where oxygen deficient media results in favorable conditions for undesirable microbial growth, as well as for pre-harvest and post-harvest crop maintenance. However, it is critical that the preservative constituents of the composition do not interfere with plant growth, development, and/or quality. Free oxygen radicals, for example, which may have biocidal activity, can underlie basic plant signaling and stress responses [Demidchik et al., *Free oxygen radicals regulate plasma membrane $Ca^{2+}$- and $K^+$-permeable channels in plant root cells, J. Cell Science* 116(1):81-88 (2003)], and their reaction products can inhibit plant growth [Date et al., *Effects of chloramines concentration in nutrient solution and exposure time on plant growth in hydroponically cultured lettuce, Scientia Horticulterae* 103 (3):257-265 (2005)].

SUMMARY OF THE INVENTION

The present invention provides nutrient compositions that deliver active oxygen and/or radical species, the nutrient composition having microbiocidal properties without inhibiting plant growth and/or development, and/or without negatively impacting crop health or quality.

In one aspect, the present invention provides nutrient compositions that are oxygen-enriched, and potassium-based. The nutrient compositions generally comprise hypochlorous acid and potassium salts to promote plant or crop growth, health, and/or quality. The composition may be used for seed treatment and germination and for applying to crops, including vegetables, fruits, flowers, potted plants, grains, cereals, animal feeds, tobacco plants, and other plants and trees. The composition may be employed for crops grown in greenhouses, including hydroponic facilities, nurseries, farms, and any other indoor or outdoor facilities.

In various embodiments, the nutrient composition comprises a solution that is generated through electrochemical treatment of potassium chloride or a combination of potassium chloride (KCl) with potassium or sodium carbonate or bicarbonate ($K_2CO_3$, $Na_2CO_3$, $KHCO_3$, $NaHCO_3$), or other carbonate salt, and/or potassium phosphate(s). For example, in various embodiments, the electrochemical feed solution comprises KCl in an amount of from about 0.2 g/L, up to saturated potassium chloride. The feed solution may comprise KCl in the range of from about 0.2 g/L to about 200 g/L, 0.2 g/L to about 20 g/L, or from about 0.2 g/L to about 10 g/L, or from about 0.2 g/L to about 5 g/L, or from about 0.2 g/L to about 1.5 g/L. In some embodiments, the electrochemical feed solution may comprise one or more of potassium bicarbonate, sodium bicarbonate, potassium carbonate, sodium carbonate, or other carbonate salt, and potassium phosphate (collectively) at from about 0.2 g/L to about 5 g/L, or in some embodiments, from about 0.5 g/L to about 3 g/L. The potassium and/or sodium bicarbonate may act to stabilize the electrolyzed solution in some embodiments, which is particularly beneficial where the solution is not generated at the point of use.

The feed solution may be processed through an electrolytic cell to produce an electrochemically-treated solution. The solution produced by electrochemical treatment has a predetermined salinity level, pH and concentration of oxidants measured as free available chlorine (AFC). As a result of the electrochemical process of KCl (alone or with the addition of other electrolytes), dilute nutrient solutions with targeted pH and total oxidants, measured as AFC, are produced.

In some embodiments, a 1× nutrient solution comprises at least 98.7% or at least 99.8% by weight water, no more than 0.2% or no more than 0.1% by weight potassium chloride, no more than 1% or no more than 0.1% by weight hypochlorous acid, and up to 0.003% by weight dissolved oxygen. The pH range is from about 3.5 to about 9.0, and the oxidant content is from about 5 to about 10,000 ppm. In some embodiments, the oxidants content is from about 5 to about 1000 ppm, but in other embodiments, is from 1000 to about 10,000 ppm. The oxidants include, but are not limited to, hypochlorous acid, dichlorine monoxide, oxygen, and bicarbonate and peroxicarbonate radicals. In certain embodiments, the solution is prepared as a concentrated commercial preparation, which is diluted before application to the plant or crop.

In still other aspects of the invention, the nutrient composition is a clay-based potassium-enriched nutrient formulation, having antimicrobial activity for agricultural applications. The composition comprises the electrochemical solution together with a clay-based carrier composition, thereby providing the desired viscosity as well as macroelements and micronutrients for plant growth or health.

The nutrient composition or solutions may be directly applied and/or indirectly to the plant, plant part, tuber, or seed using any suitable device, such as a spraying, fogging, or drenching device. Indirect application includes but is not limited to applying the composition or solutions to the area around the plant, such as to the growth media in which the plant is situated (e.g., the soil around a plant in a field situation).

The composition and electrolyzed solution provide for oxidation of water impurities, including hydrogen sulfide, iron, manganese and organic contaminants. The nutrient solution may be effective to enhance plant growth and seed germination by providing a nutrient source containing growth promoting elements, including oxygen and potassium, and may be effective to promote plant and seed health by stimulating their immune system to fight infection. The nutrient composition or solution may also be effective to prevent or reduce the risk of plant disease from water and airborne plant pathogens through irrigation water, and/or effective to enhance seed germination rate by disinfecting microbial pathogens, and/or effective to prevent build up of microbial biofilms and spread of mildew in water irrigation systems, including sprayers, waterlines and tanks, and/or effective to increase the amount of water that can be recycled in closed irrigation systems by reduction of the build-up of biofilm and waterborne pathogens.

In another aspect, the invention provides methods for growing, caring for, and preserving plants and/or plant parts, such as cut flowers, by applying the composition or solution of the invention to plants or plant parts. Alternatively or in addition, the solution is applied to propagation material to protect it from disease and/or enhance plant growth and/or plant development and/or plant health. In certain embodiments, the nutrient composition or solution is used to support hydroponic plant growth. For example, the nutrient solution either alone or in combination with other active ingredients are cycled continuously or intermittently through a hydroponics system. The disease protection and/or enhanced plant growth, development and/or health realized by using the compositions and methods of the present invention may lead to improvements in plant performance including but not limited to obtaining greener plants, greater yield, better standability, less root lodging and/or less fruit rotting.

In still other embodiments, the nutrient composition is applied to protect or enhance the plant or crops post-harvest. In various embodiments, the nutrient compositions or solutions are applied for the prevention and control of post-harvest rotting and contamination of fruit, vegetables and plants.

In another aspect, the invention provides a method for preparing the oxygen enriched potassium-based nutrient solution or composition for supporting plant or crop production. The method involves incorporating carbonate or bicarbonate (as described) into KCl electrolyte for electrochemical treatment, or incorporating directly into an electrolyzed solution of KCl comprising hypohalous acid (e.g., HOCl).

DESCRIPTION OF FIGURES

FIG. 2 shows treatment of wheat seed prior to germination.

FIG. 4 shows the results of tomato seed treatment prior to germination, using a clay-based hypochlorous acid composition.

DETAILED DESCRIPTION OF THE INVENTION

Figure 1:
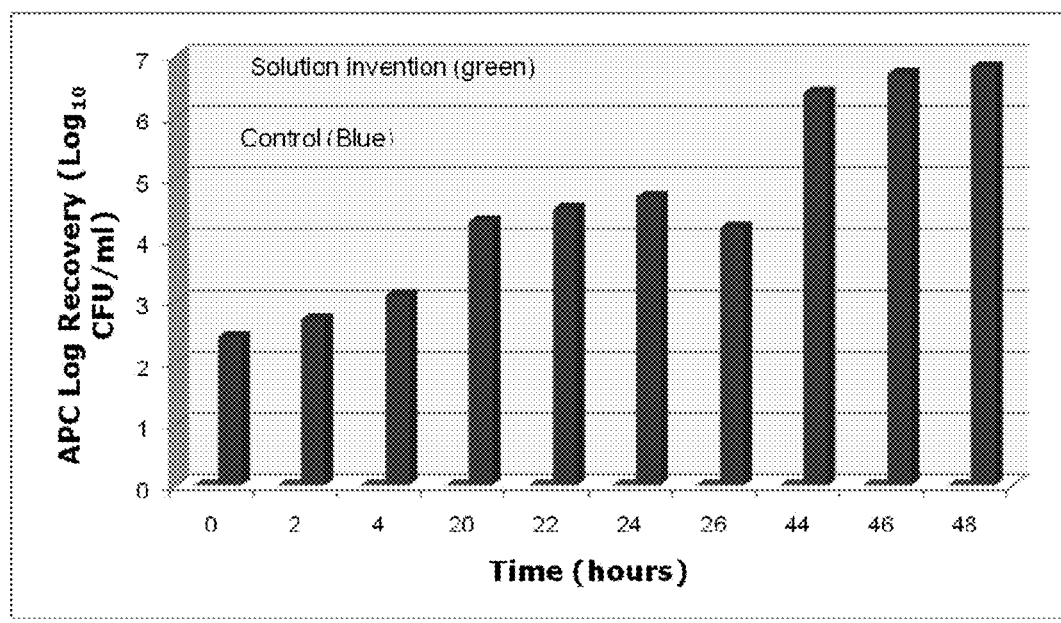
FIG. 1 shows the reduction in growth of a microbial plant pathogen by an exemplary embodiment of a nutrient solution according to the invention. Bars on left represent the hypochlorous acid solution, with the controls on the right.

The invention relates to nutrient compositions for agricultural applications, and methods for plant or crop growth and care. The nutrient composition comprises a potassium-based nutrient solution enriched by electrochemical treatment, and optionally a carrier composition. In various embodiments, the potassium-based nutrient composition comprises hypochlorous acid. The present invention involves the use of the nutrient compositions or solutions, among other things, in pre-harvest and post-harvest treatments and in environmental and soil disinfection.

In one aspect, the present invention provides nutrient compositions that are oxygen-enriched, and potassium-based, and comprise hypochlorous acid and potassium salts to promote plant or crop growth, health, and/or quality. In various embodiments, the composition promotes plant or crop growth through various stages of development, and/or reduces or eliminates the risk of airborne and waterborne anaerobic bacteria, as well as mold and fungal diseases of plants. Particularly, the combination of oxygen and hypochlorous acid provides antimicrobial properties to the nutrient composition, and in combination with potassium, induces systemic protection and modifies disease resistance or susceptibility of crops to infections. In certain embodiments, the composition reduces water intake without negatively affecting the plants, thereby helping to reduce water needs, which in turn provides savings on costs and labor. Further still, the composition helps to control undesirable odors in certain embodiments.

The composition may be used for seed treatment and germination and for applying to crops, including vegetables, fruits, flowers, potted plants, grains, cereals, animal feeds, tobacco plants, and other plants and trees. These crops may be grown in greenhouses, including hydroponic facilities, nurseries, farms, and any other indoor or outdoor facility.

In various embodiments, the nutrient composition comprises a solution that is generated through electrochemical treatment of potassium chloride or a combination of potassium chloride (KCl) with potassium or sodium carbonate/bicarbonate, and/or potassium phosphate(s). In a certain embodiments, the composition is based on a solution prepared by electrochemical treatment of a KCl solution with one or more (or all) of $K_2CO_3$, $KHCO_3/KCO_3$, $NaHCO_3/NaCO_3$, $Na_2CO_3$, $K_3PO_4$, $KH_2PO_4$, and $K_2HPO_4$. Other electrolytes, or salts may be included as well as additional ingredients desired to support plant growth or control microbial growth or pests. The properties of the nutrient composition or solution, such as pH, total dissolved solids, and oxidant content are controlled by the regimen of electrochemical treatment. The solution may be subject to further dilution and additional chemicals, such as for example, wetting agents, to achieve optimal solution composition, and to provide oxidation, fungicidal, or biocidal activity for surface decontamination in addition to water quality control.

The feed solution for electrochemical treatment may comprise KCl in an amount of from about 0.2 g/L, up to saturated potassium chloride. For example, in some embodiments, the feed solution may comprise KCl in the range of from about 0.2 g/L to about 200 g/L, or about 0.2 g/L to about 20 g/L, or about 0.2 g/L to about 10 g/L, or about 0.2 g/L to about 5 g/L, or about 0.2 g/L to about 3 g/L. In certain embodiments, the feed solution comprises saturated potassium chloride. In certain embodiments, the feed solution comprises KCl at from about 0.5 g/L to about 20 g/L or about 0.5 g/L to about 5 g/L. In some embodiments, the feed solution is a mixture of potassium chloride-based electrolyte with a diluted solution of potassium carbonate (and/or sodium carbonate), and optionally potassium phosphate. For example, the feed solution may comprise, in addition to KCl: $K_2CO_3$, $KHCO_3$ (and/or $NaHCO_3$), and in addition may comprise $K_3PO_4$, $KH_2PO_4$, and $K_2HPO_4$. When KCl is mixed with another electrolyte (e.g., NaCl), preferably, KCl is the predominant salt. For example, the feed solution has more KCl than any other electrolyte. In certain embodiments, the feed solution comprises potassium carbonate (and/or sodium carbonate) and/or potassium phosphate (collectively) at from about 0.2 g/L to about 5 g/L, or in some embodiments, from about 0.5 g/L to about 3 g/L. Addition of potassium carbonate (and/or sodium carbonate) and/or potassium phosphate (collectively) directly effects oxygen enrichment level in the nutrient solution produced through a diaphragm based electrolytic cell. In some embodiments, potassium and/or sodium carbonate or bicarbonate are included at an amount that stabilizes the solution, which is particularly beneficial where the solution is not generated at the point of use.

Without being bound by theory, dissolved inorganic carbon (DIC), which generally includes carbonates, bicarbonates, carbonic acid and dissolved $CO_2$, provides low or minimal buffering capacity in the pH range targeted by the solutions and compositions described herein. Nevertheless, these solutions are effectively stabilized, such that the solutions and compositions are not dependent on "on-demand" production. The stabilizing effect can be due to, in-part, free radical scavenging ability of DIC to thereby slow the decomposition of HOCl.

The feed solution may be processed through an electrolytic cell to produce the electrochemically-treated solution. A diaphragm-based electrolytic cell, may be used for the electrochemical treatment; however, other electrolytic cells with separated anode and cathode chambers may be employed. For example, the Sterilox® 2200, or Sterilox® 2300 may be used for the electrochemical treatment. Methods of operating electrochemical cells are disclosed in U.S. Pat. Nos. 7,303,660, 7,828,942, 6,770,593 and 7,335,291, 7,897,023, as well as WO 2004040981, each of which are hereby incorporated by reference in their entireties. Such methods may be employed here.

The solution produced by electrochemical treatment has a predetermined salinity level, pH, and concentration of free available chlorine (AFC). As a result of the electrochemical process of KCl alone or with the addition of the salts (as described), diluted (i.e., below 1.5 g/L of total dissolved solids) nutrient solutions with targeted pH and total oxidants, measured as AFC, are produced. Dissolved oxygen content may reach from 130 to 300% saturation in case of addition of potassium carbonate (and/or sodium carbonate) and/or potassium phosphate (collectively), such as from 130% to about 200% in case of carbonates or carbonates additives to precursor solution.

The solution in certain embodiments, employs a stabilizing amount of a bicarbonate or carbonate of alkali or alkaline earth metal, such as, for example, sodium, potassium, calcium, or magnesium. In some embodiments, the bicarbonates or carbonates are added prior to the formation of hypohalous acid (e.g., by electrochemical treatment), and in other embodiments, the bicarbonates or carbonates are added to the solution after formation of hypohalous acid. For example, the bicarbonate(s) or carbonate(s) may be added to the precursor solution, the electrolyte, and/or the end solution.

The carbonates and bicarbonates may be added at a "stabilizing amount," which can be determined with reference to the change in the pH or AFC content of the solution over time. Generally, the solution is considered stabilized if the amount of AFC does not drop below about 75% of the initial value over a period of about 6 months. In certain embodiments, the AFC content is stabilized for at least one year from the production date of the solution. Further, the stability of the solution may be determined with reference to the pH. Generally, the solution is considered stabilized if the pH does not vary by 1 unit over a period of about 6 months. In certain embodiments, the pH is stabilized for at least one year from the production date of the solution. The solution should be stored at 20° C. or less for greater stability. 20° C. is the reference temperature for determination of stability. The solution should be stored in storage containers which are non-permeable by mean of UV light and diffusion of dissolved gasses.

The stabilizing amount of carbonate or bicarbonate can be determined with reference to the AFC content. For example, the stabilizing amount of the carbonate or bicarbonate is incorporated into the solution at a molar ratio of about 1:2 with respect to the AFC level. In some embodiments, the bicarbonates or carbonates are incorporated into the solution in at least equimolar amounts with respect to the AFC content (e.g., hypochlorous acid content). In still other embodiments, the bicarbonate/carbonate is incorporated at 2:1, 5:1 or more with respect to AFC content. In some embodiments, other components that may affect the AFC content, such as phosphate buffers, are not employed or are present in limited amounts.

For example, for solutions having an AFC content of from about 200 ppm to about 500 ppm, carbonate or bicarbonate may be incorporated at an amount of from about 300 mg/L to about 1500 mg/L to stabilize the solution. In certain embodiments, such solutions are stabilized by incorporating from about 400 to about 1000 mg/L of carbonate or bicarbonate. In some embodiments, the addition of the bicarbonates or carbonates of alkali or alkaline earth metals provide for enhanced biocidal effectiveness, especially in the presence of high organic load.

In some embodiments, the nutrient solution (1× concentration) comprises at least 98.7% (e.g., at least 99.8%) by weight water, no more than 0.2% (e.g., no more than 0.1%) by weight potassium chloride, no more than 1% (e.g., no more than 0.1%) by weight hypochlorous acid, and up to 0.003% by weight dissolved oxygen. The pH range is from about 3.5 to about 9.0, and from about 4.0 to 8.0 in certain embodiments, and the oxidant content is from about 1 to about 10,000 ppm. For example, in certain embodiments where high oxidant content is preferred, the solution may have from 200 ppm to about 10,000 ppm, or about 400 ppm to about 6,000 ppm, about 600 ppm to about 2000 ppm, or about 800 ppm to about 1000 ppm. Where low oxidant content is preferred, the solution may have from 1 ppm to about 200 ppm, 5 ppm to about 100 ppm, 10 ppm to about 50 ppm, or from 1 ppm to about 20 ppm, or from about 1 ppm to about 10 ppm. The oxidants include, but are not limited to, hypochlorous acid, dichlorine monoxide, oxygen, and bicarbonate and peroxicarbonate radicals.

In some embodiments, the nutrient solution is prepared by electrochemical treatment of NaCl, with post-process addition of $K_2CO_3$, $KHCO_3$, $NaHCO_3$, $KH_2PO_4$, and/or $K_2HPO_4$. In some embodiments, electrochemical treatment of a NaCl solution is conducted as described in U.S. Pat. No. 7,897,023, which is hereby incorporated by reference in its entirety.

In some embodiments, other compositions are incorporated to achieve the desired properties, including viscosity. For example, a clay-based agent or carrier is added post electrolysis to enhance solution properties in some embodiments. The addition of the clay ingredient enhances the properties of the formulation by extending the residual antimicrobial activity and delivering macro- and micro-nutrients. The clay materials are generally compatible with the solution and enhance the viscosity. Additional benefits according to these embodiments include prolonged antifungal activity due to enhanced residual effect on the plant surface, enhanced inhibition of fungal spore adhesion and prevention of fungal infection, and addition of nutrients or macro elements to enhance growth.

Clay compositions and formulations are well known in the art and may comprise micronutrients such as iron, zinc, copper, manganese, molybdenum, and boron, as well as macronutrients such as nitrogen, phosphorus and lithium. Exemplary compositions that may be used in accordance with the invention are described in U.S. Pat. No. 8,017,158, U.S. Pat. No. 7,906,131, U.S. Pat. No. 7,080,481, U.S. Pat. No. 6,939,357, each of which are hereby incorporated by reference. In some embodiments, the carrier composition comprises one or more of kaolin clay, laponite clay, aluminum oxide, zinc oxide, and aluminum silicate. Compositions and formulations may comprise optimal amounts of silica, calcium, magnesium, and sulfur, including calcium silicate and magnesium sulfite. In some embodiments, the electrochemically treated nutrient solution is incorporated as a slurry with a clay material (e.g., from 2% to 50% by weight clay, or from 5% to about 40% by weight clay, or from 10 to 30% by weight clay), such as a kaolin or laponite clay. In some embodiments, the electrochemically treated nutrient solution is incorporated as a sol with a silica-based clay material (e.g., from 0.5% to about 2% by weight clay, such as a laponite clay). The composition in some embodiments has a viscosity in the range of about 5 cp or 10 cp to about 2,000 cp, or in other embodiments, from about 10 cp to about 5000 cp. In some embodiments, the viscosity may be in the range of about 20 cp to about 500 cp, or about 20 cp to about 100 cp.

While the solution may comprise, or consist essentially of hypochlorous acid as the active agent, in some embodiments, the solution may contain other hypohalous acids (e.g., HOBr, or mixture thereof). In some embodiments, the solution contains other oxidizing or radical producing species such as a hypochlorite, hydroxide, $H_2O_2$ and $O_3$, among others.

The properties of the nutrient solution are tailored to the application requirements. For example, for pre-treatment of seeds prior to their germination (e.g., according to the methods described herein), the solution has a high oxidants content of greater than 400 ppm or greater than 500 ppm. For example, the oxidants content can be in the range of 500 ppm to 1200 ppm in various embodiments (e.g., about 1000 ppm, or from about 800 to about 1200 ppm) and a pH in the range of 4-6 (e.g., about 5, or 4.5 to 5.5). In other embodiments, the solution has an oxidants content of up to about 10,000 ppm, for example, when applied as a mist for foliar shock treatment or as an irrigating water additive for foliar treatment. Depending on the type of seeds and their sensitivity to moisture, the seeds may be rinsed or fogged with the nutrient solution, or submerged in the nutrient solution. At the stage of seed germination, the solution has a relatively low oxidants content, e.g., about 1 to about 5 ppm, and a pH of about 7 to about 8. At the stage of plant growth, the solution may have low oxidants, e.g., at about 1 to about 5 ppm, and the total dissolved solids and pH value of the applied solution are dictated by the type of plant being treated, and in various embodiments involves a pH of about 5.8 to about 7.5, and electro-conductivity of about 1.5 to 3 mS/cm.

Parameters of nutrient solution, such as pH, total dissolved solids and oxidants content are controlled by the regime of treatment. Systems described herein provide the ability to produce solutions within a pH range from 3.5 to 9 and total oxidants content from 5 to 10,000 ppm.

Without wishing to be bound by theory, the composition and solution of the invention provides for oxidation of water impurities, including hydrogen sulfide, iron, manganese and organic contaminants. The nutrient solution may be effective to enhance plant growth and seed germination by providing a nutrient source containing growth promoting elements, including oxygen and potassium, and may be effective to promote plant and seed health by stimulating their immune system to fight infection. The nutrient composition or solution may also be effective to prevent or reduce the risk of plant disease from water and airborne plant pathogens through irrigation water, and/or effective to enhance seed germination rate by disinfecting microbial pathogens, and/or effective to prevent build up of microbial biofilms and spread of mildew in water irrigation systems, including sprayers, waterlines and tanks, and/or effective to increase the amount of water that can be recycled in closed irrigation systems by reduction of the build-up of biofilm and waterborne pathogens.

The nutrient composition or solutions may be directly and/or indirectly applied to the plant, plant part, growth media, tuber, or seed using any suitable device, such as a spraying, fogging, or drenching device. In certain embodiments, the solution is prepared as a concentrated commercial preparation (concentrated with respect to the solution properties disclosed herein), which is diluted before application to the crop. For example, the commercial preparation may be diluted 5-fold, 10-fold, 100-fold, or 200-fold or more prior to use. Concentrated commercial formulations may be supplied in bottled form, and where stabilized as described herein, may have a shelf-life of one year or more. Preparations of stabilized hypochlorous acid solutions are further described in U.S. 2012/0232616, which is hereby incorporated by reference.

The stabilized solutions (including concentrated forms) may be packaged for storage or sale, using any suitable container, such as any suitable plastic or glass bottles, or bags (e.g., plastic bags). The containers may be transparent, or opaque so that they are impenetrable by light, and may be of any unit volume, such as about 100 ml, about 125 ml, about 250 ml, about 0.5 liter, about 1 liter, about 5 liters, about 20 liters, or greater.

The nutrient solutions may be used in commercially available formulations, or as a mixture with other active compounds, such as growth-regulating substances, fertilizers, fungicides, bactericides, insecticides, nematicides, acaricides, sterilizing agents, attractants, or semiochemicals.

In another aspect, the invention provides methods for growing, caring for, and preserving plants and/or crops, by applying the composition or solution of the invention to plants, plant parts, and/or the areas around such plants and/or plant parts. Virtually any plant can be treated with the nutrient composition according to this aspect of the invention to promote growth and prevent or lessen many plant diseases. Treatment can be to individual plant parts, plant tissue cultures, individual plants, groups of plants or to whole fields of crop plants. For example, in various embodiments the solution is applied to one or more of potato plants, tomato plants, sugar beets, canola, strawberries, chick peas, lentils, broccoli, asparagus, cabbage, cauliflower, turf grass, tobacco, spinach, carrots, ginseng, radish, cotton, soybeans, corn, rice, wheat, field peas, apple trees, orange trees and ornamental plants, including poinsettias, petunias, and roses, or their roots, rhizomes, tubers, corms or seeds and the like. Alternatively or in addition, the solution is applied to propagation material of any of the foregoing to protect from disease and enhance growth and/or development.

The nutrient compositions or solutions may be applied by spray or atomized foliarly or applied in-furrow at the time of planting or after planting during the growth of the plant, either separately or mixed together with other active compounds at the time of application. For example, the nutrient composition or solution either alone or in combination with other active compounds may be introduced to the soil either before germination of the seed or afterwards directly to the soil in contact with the roots. Methods for applying the solutions to the soil include any suitable method that ensures that the nutrient solution penetrates the soil, for example, nursery tray application, in furrow application, soil drenching, soil injection, drip irrigation, application through sprinklers or central pivot, and incorporation into soil (broad cast or in band).

In various embodiments, the nutrient solution is applied for treatment and control and/or prevention of fungal and bacterial diseases including *Rhizoctonia* spp. (e.g., *Rhizoctonia solani*), *Pythium* spp. (e.g., *Pythium ultimum*), *Fusarium* spp., *Verticillium* spp., *Alternaria* spp. (e.g., *Alternaria solani, Alternaria brassicicola*), *Phytophthora* spp. (e.g., *Phytophthora infestans*), *Aphanomyces, Cercospora, Rhizopus, Sclerotium, ergot, Ascochyta, Anthracnose, Phytoph-*

*thora infestans, Pythium ultimum, Botrytis cinerea, Colletotrichum cocodes, Cladosporium cucumerinum, Monilinia fructicola, Venturia pyrina, Acidovorax avenae, Pseudomonas syringae, Xanthomonas campestris, Erwinia carotovora, Clavibacter michiganense, Plasmopara viticola, Sphaerotheca fuliginea, Uncinula necator*, and *Peronospora parasitica*.

In certain embodiments, the nutrient composition or solution is used to support hydroponic plant growth. Hydroponics is a method of growing plants using mineral solutions without soil. For example, terrestrial plants may be grown with their roots in the mineral nutrient solution alone or with an inert medium, such as gravel, rock wool (mineral wool), brick shards, pozzolanic lassenite, baked clay pellets, polystyrene peanuts, coconut husk, pumice, wood fiber, vermiculite, or perlite. In a hydroponics system, the plants absorb essential minerals as inorganic ions directly from the water, and soil is not required for plant growth.

Odor management and water management continue to be problems in hydroponics. The nutrient solutions described herein may decrease water intake without negatively affecting plants and also reduce water needs in case of water recycling, thus providing saving on costs and labor. The nutrient solutions of the present invention can also be used to control undesirable odors.

Thus, in various embodiments, the present invention involves using the nutrient solutions either alone or in combination with other active ingredients in a hydroponics system to provide nutrients to the plants and to control bacterial and/or fungal growth and associated odors. For example, the nutrient solution either alone or in combination with other active ingredients are cycled continuously or intermittently through the hydroponics system. In certain embodiments, the nutrient solutions either alone or in combination with other active ingredients are cycled through a hydroponics system intermittently, for example, at the beginning of a new planting of crops, during the growth period of the crops, and/or at the end of the growth period of the crops at or near the time of harvest. Alternatively, the nutrient solution is cycled through the hydroponics system about once per day, once per week, or about once per month. Thus, in various embodiments, the solution or composition of the invention is applied from once to about ten times per month. In one embodiment the nutrient solutions either alone or in combination with other active ingredients are applied as a foliar spray to the plants in the hydroponics system.

In one embodiment, the nutrient solutions are introduced into the hydroponic system to treat plant diseases common to hydroponics systems, including but not limited to damp-off due to *Verticillium* wilt; root rot often caused by *Phytophthora* spp.; crown and stem rot often caused by *Fusarium* spp.; damping off caused by *Botrytis, Macrophomina phaseoli, Phytophthora, Pythium, Rhizoctonia solani, Sclerotium rolfsii*, or *Thielaviopsis*; clubroot caused by *Plasmodiophora brassicae*; powdery mildew caused by fungi in the order Erysiphales; early blight caused by *Alternaria solani*; and rusts caused by fungi in the order Pucciniales. Where evidence of such pathogens or diseases are apparent, the solution may be applied as described above to reduce or control the disease.

In still other embodiments, the nutrient composition is applied to protect or enhance the plant or crops post-harvest, e.g., from the time after harvest and through transport for sale to consumers. Appropriate control of diseases that affect harvests during handling in the field as well as rotting during post-harvest storage is critical to minimizing the loss of marketable crops. Approximately 15% of total agricultural production in developed countries is lost for these reasons. Post-harvest disease is an even greater problem in developing countries where it can account for as much as 40% in total production. For example, crops such as spinach, lettuce, alfalfa sprouts, parsley, cilantro, citrus, strawberries, bananas, peaches, and mangoes often become biologically contaminated post-harvest. Contamination can be initiated pre-harvest (e.g., by parasitic presence at the time of picking/harvesting), during harvesting (e.g., when contaminants are introduced by human intervention or mechanical harvesters) and post-harvest (e.g., where spores and parasites settle on harvested produce). The biological contamination can be caused by fungus, mold or bacteria that damage the crops and lead to losses in the production of marketable produce. Worse yet, the biological contamination can be caused by organisms that are pathogenic to humans, including *Escherichia coli* and *Salmonella*. If this type of contamination goes undetected, and the contaminated crops are consumed, an outbreak of human disease may result.

Accordingly, in various embodiments, the nutrient compositions or solutions are applied for the prevention and control of post-harvest rotting and contamination of fruit, vegetables and plants. In one embodiment, the nutrient solutions may be sprayed or fogged onto the fruit, vegetables or plants. In another embodiment, the fruit, vegetables or plants are submerged in the nutrient solutions. The present invention in another embodiment provides for submersion of the harvested fruit, vegetable, plant, or a part thereof, in the nutrient solution to maintain the harvested fruit or vegetable in a hydrated and disease-free state. In certain embodiments, harvested fruit, vegetables and plants are treated as described above prior to transportation and storage to eradicate any such biological contamination or live pests.

In another aspect, the invention provides a method for preparing the oxygen enriched potassium-based nutrient solution or composition. The method involves incorporating carbonate or bicarbonate (as described) into KCl electrolyte for electrochemical treatment, or directly to an electrolyzed solution of KCl comprising hypohalous acid (e.g., HOCl). For example, an electrolyzed solution or other hypohalous acid solution may be diluted with water or aqueous solution comprising bicarbonates or carbonates. In other embodiments, the diluted hypohalous acid solution (e.g., having the desired AFC content) is added to containers comprising dry bicarbonates or carbonates of alkali or alkaline earth metals.

The carbonate or bicarbonate can be added to the dry electrolyte in accordance with the desired AFC content of the resulting solution. Hypochlorous acid solutions may be prepared by passing KCl solution containing the carbonate/bicarbonate over coated titanium electrodes separated by a semi-permeable ceramic membrane at a current of about 6 to 9 Amps. Electrochemical treatment of saline is described, for example, in U.S. Pat. No. 7,303,660, U.S. Pat. No. 7,828,942, and U.S. Pat. No. 7,897,023, which are hereby incorporated by reference.

Carrier compositions, such as clay-based carriers, as already described, can then be incorporated.

The following non-limiting examples illustrate certain embodiments of the invention.

EXAMPLES

Example 1

Bactericidal and Fungicidal Activity of Oxygen-Enriched Potassium-Based Hypochlorous Acid Oxygen-enriched potassium-based solution of hypochlorous acid was produced by processing KCl, 2 g/l, through a diaphragm based electrolytic cell. Solutions with final pH of 5.75-6.75 and 200±20 ppm oxidants content were produced by adjusting a catholyte partial discharge and recirculation through the anode chamber. Dissolved oxygen saturation varied from 130 to 160%. The conductivity of the nutrient solution varied from 1.5 to 3.0 mS/cm depending on the solution pH. Produced solutions were tested for bactericidal action.

The bactericidal action of the solution of the invention (at a hypochlorous acid concentration of 200 ppm AFC and a pH range of 5.75-6.75) when sprayed (fogged) was assessed against a species of the crop pathogen *Pseudomonas*, which was spotted at $10^{8.4}$ CFU on ceramic tiles of 10×10 cm$^2$ and placed at various positions, both vertically or horizontally within rectangular areas of 50 cm×30 cm. After spraying with solution of the invention and 1 h of settling, *Pseudomonas* counts on all carriers were always found to be below detection limits (2 $\log_{10}$ CFU/ml). These results show that the solution when sprayed produced reductions of greater than 6 $\log_{10}$ CFU/ml against a species of *Pseudomonas*, as compared to tiles that were not treated with the electrolyzed solution.

The antifungal activity of the solution (at a hypochlorous acid concentration of 180 ppm AFC and a pH range of 5.75-6.75) was tested against species of two fungal crop pathogens *Candida* and *Aspergillus* in laboratory tests. Fungal suspensions (1 ml) were added to 1 ml of sterile distilled water and 8 ml of the electrolyzed solution was added at a range of concentrations at 20° C. After exposure times of 5 mins, 1 ml samples were neutralized using a standard quench solution. All samples were serially diluted, plated out on Tryptic Soy Agar, incubated at 37° C. for 3 days and colony forming units counted. Results show that the solution produced greater than a log 4 kill against both fungal crop pathogens within 5 minutes (See Table below).

| Test organism | Control Reduction in surviving cells | Electrolyzed Solution Reduction in surviving cells |
|---|---|---|
| *Candida albicans* ATCC 10231 | <10$^2$/5.0 | >10$^4$/1.0 |
| *Aspergillus niger* ATCC 16404 | <10$^2$/5.0 | >10$^4$/1.7 |

Example 2

Oxygen-Enriched Potassium-Based Solution of Hypochlorous Acid for Control of Plant Pathogens Oxygen-enriched potassium-based solution of hypochlorous acid was produced by processing KCl through a diaphragm based electrolytic cell. Solutions with a final pH of 5.8±0.2, 50 ppm of oxidants content, and 138% saturation of dissolved oxygen were tested for microbial cross-contamination prevention through the water.

The ability of the solution (at a hypochlorous acid concentration of 50 ppm AFC and a pH range of 5.6-6.1) to control microbial growth of plant pathogens in water was evaluated in laboratory tests. Asparagus bunches were stored in either the electrolyzed solution or tap water over 48 hours and the level of growth of Enterobacteriaceae bacteria in the storage solutions was measured. Enterobacteriaceae are a family of bacteria of great importance since Enterobacteriaceae include important plant pathogens, such as *Erwinia, Pantoea, Pectobacterium* and *Enterobacter*. Results showed that using the electrolyzed solution to store asparagus prevented the growth of Enterobacteriaceae during 48 hours of storage. The tap water control used to store asparagus became contaminated with Enterobacteriaceae after 2 hours at room temperature and showed heavy contamination of 50,000 CFUs per ml of Enterobacteriaceae after 24 hours and more than one million CFU per ml after 48 hours (see FIG. 1).

Example 3

Pretreatment of Seeds Prior to Germination

A mixture of 2 g/l of KHCO$_3$ and 8 g/l of KCl were used as a feeding electrolyte solution processed through the diaphragm based electrolytic cell. The final nutrient solution had a pH 5.8, electro-conductivity 1.88 mS/cm, oxidants content of 500 ppm (measured as available free chlorine), and 208% saturation of dissolved oxygen.

Non-diluted solution was used for pre-treatment of Persian Baby cucumber seeds prior to germination. 6 packs of commercially available seeds were treated for 4 hours in test solutions. The germination of the pre-treated seeds was compared to the non-treated seed germination. The samples germination were tested after 3 days for early counts and after seven days for final counts. The results showed early germination of the pre-treated seeds in comparison to non-treated seeds.

| Seeds exposure time to nutrient solution, hrs | 3 days early germination count (%) | 7 days final count (%) |
|---|---|---|
| 0 (control) | 43 | 97 |
| 4 hours (test) | 67 | 99 |

Example 4

Oxygen-Enriched Potassium-Based Hypochlorous Acid for Watering of Plants and Crops 1:100 diluted nutrient solution of the oxygen-enriched potassium-based hypochlorous acid, having 5 ppm measured as available free chlorine, was used for the watering of Poinsettia flowering potted plants. The results demonstrated better moisture content of soil, in case of watering with the solution, and better plant conditions as indicated by the appearance of the leaves and flowers, compared to the potted plants treated with water. Plants treated with water had the highest number of dry leaves.

Saturated KCl brine was used as a feeding electrolyte solution processed through the diaphragm based electrolytic cell by the method described in the U.S. Pat. No. 7,897,023. Anolyte was collected to a 20 L container comprising 20 g of dry potassium carbonate, which is equivalent to additional 390 mg/L of K$^+$ in the final nutrient. The final nutrient solution had a pH 5.4, electro-conductivity 1.88 mS/cm, oxidants content of 900 ppm (measured as available free chlorine), and 168% saturation of dissolved oxygen. Concentrate was used for the watering and spraying of the vegetable garden, by dosing it into water stream for the targeted concentration of 5 ppm AFC.

Broccoli plants were watered on a daily basis with 1:160 diluted nutrient solution of the oxygen-enriched potassium-based hypochlorous acid, having 5 ppm measured as available free chlorine. The results demonstrated consistent moisture of soil without any salt residue or mold accumulation over time.

Example 5

Clay-Based Hypochlorous Acid Compositions

The following illustrates the use of clay-based agents for seed treatment and microbial control. The following shows organic Invicta Wheat seed germination.

Oxygen enriched potassium based solution of Hypochlorous acid was produced by processing a premixed KCl, 8 g/L, and $KHCO_3$, 2 g/L, feed solution through a diaphragm based electrolytic cell. Solution with final pH range of 5.5-6.5 and concentration of free available chlorine in the range of 500-800 ppm, conductivity 1.85 mS/sm, and dissolved oxygen saturation level 130-150% was used as dispersing media in Laponite XL-21 hydrogel formulation. The final composition of HOCl+2% Laponite was used for pre-treatment of organic Invicta wheat seeds.

Figure 2A:
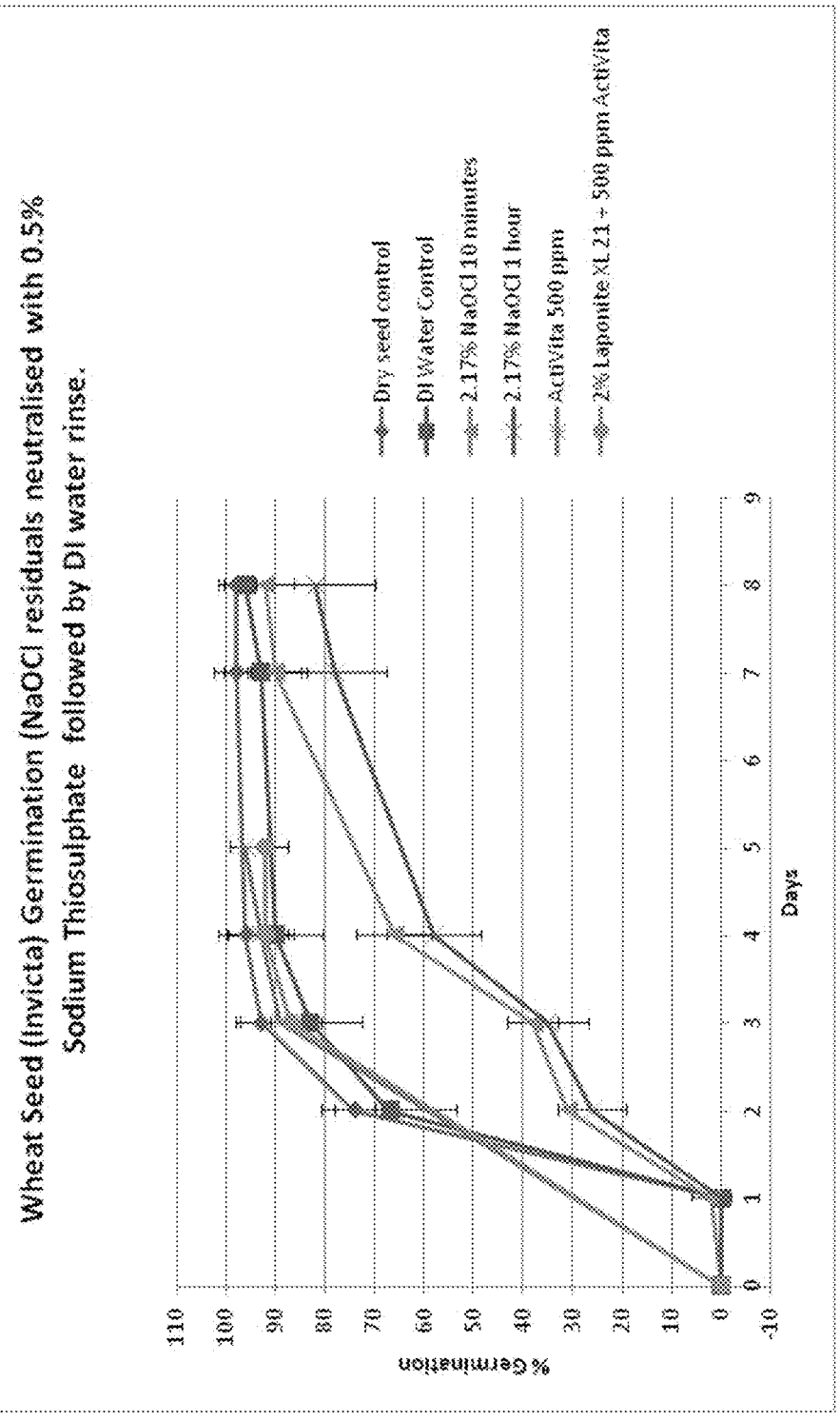
FIG. 2A shows percent germination over 8 days.
Figure 2B:
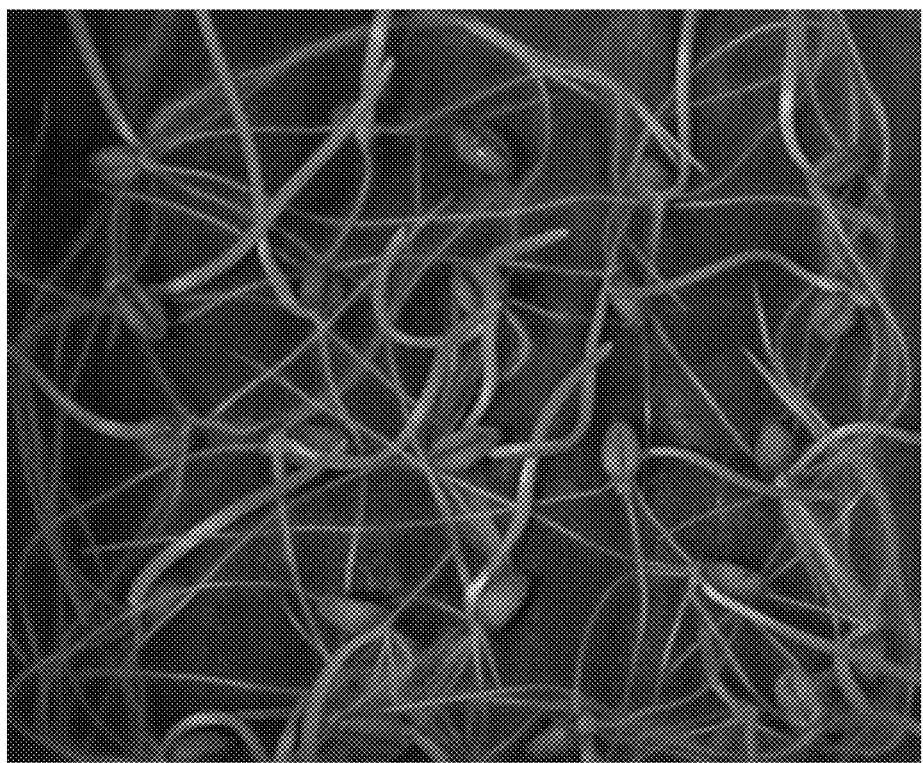
FIG. 2B shows germination after pretreatment with the hypochlorous acid solution.

The effect of the HOCl-based hydrogel on seeds germination was compared to no treatment and hypochlorite-based seed treatment. FIG. 2. The results demonstrate no significant reduction or delay on germination of organic Invicta wheat, even when potassium-enriched HOCl based hydrogel composition was left on the seeds for over 24 hours.

The following example shows microbial control of organic Invicta Wheat seeds. Organic Invicta wheat seeds were pre-treated with HOCl-LAP hydrosol composition by submerging the seeds into hydrogel and mixing by vortex for either 10 or 60 minutes. Seed:Volume ratio 20 g seed/10 ml or 20 g seed/20 ml were used as equivalent to 500 and 1000 liters/tonne of seed.

500-800 ppm of free available chlorine potassium enriched HOCl solution was applied as dispersing media for 2-2.5% Laponite hydrogel composition. These concentrations were chosen for decontaminating natural micro flora on the seed. There was no differentiation between natural microflora of the seed that was not disinfected by the composition and environmental contamination that may have infected the seeds during incubation or enumeration. Seeds dried at RT 15-20° C. for 60 hours before germination testing set up. Each composition was tested in four replicates.

Microbial Decontamination Results:

| Treatment | % infestation (48 h) | % infestation (72 h) | % infestation (96 h) | % infestation (Day 4) |
|---|---|---|---|---|
| 2% laponite + deionised water | 100 | 100 | 100 | 100 |
| 20 g seeds in 10 ml (2% LAP + 550 ppm AV); 60 min. contact time | 100 | 100 | 100 | 100 |
| 20 g seeds in 20 ml (2% LAP + 550 ppm AV) 10 min. contact time | 0 | 1 | 3 | 7 |
| 20 g seeds in 20 ml (2% LAP + 810 ppm AV) 10 min. contact time | 0 | 0 | 0 | 1 |

Figure 3:
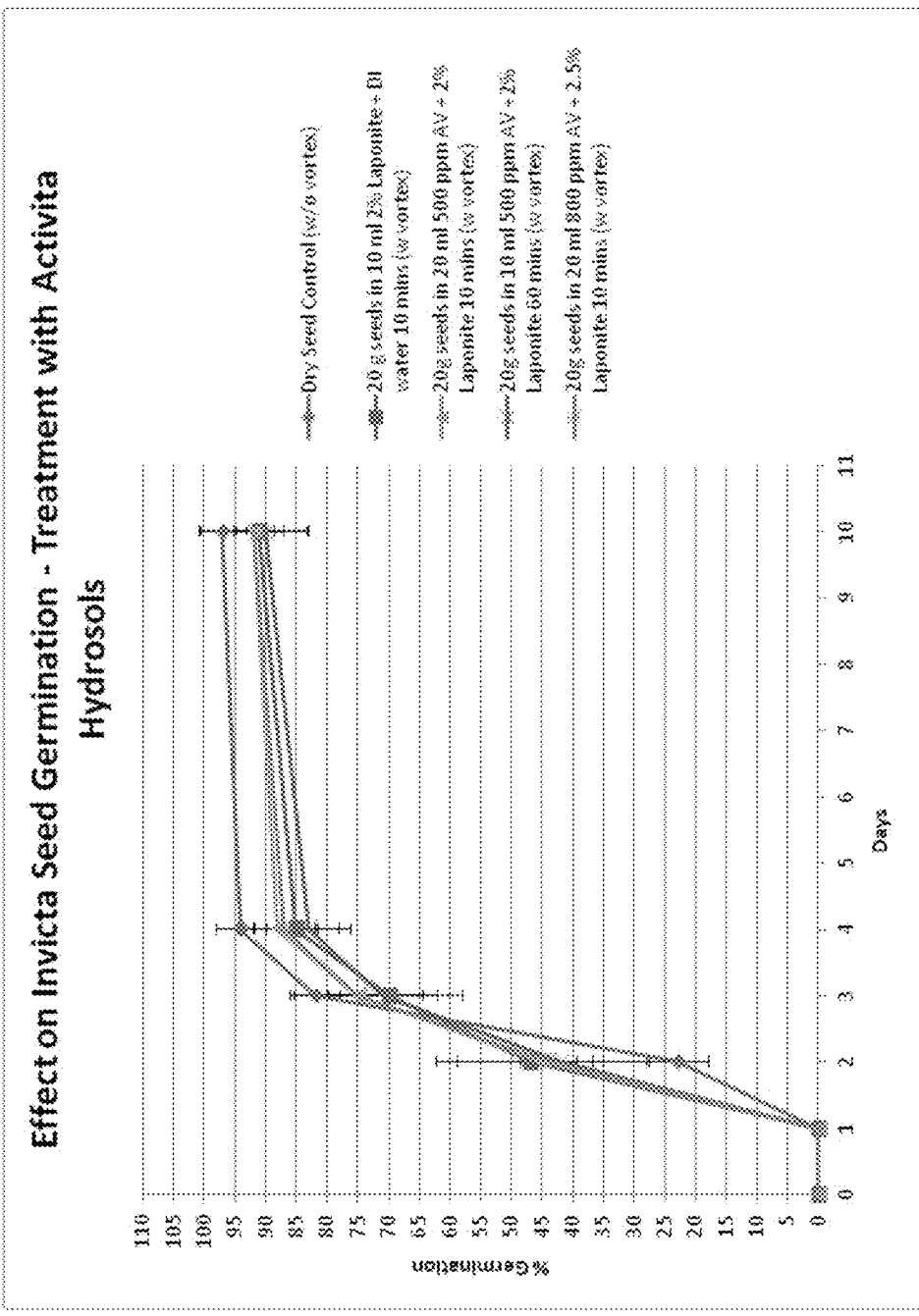
FIG. 3 shows results of wheat seed treatment prior to germination, using a clay-based hypochlorous acid composition.

The Invicta Seed germination results demonstrated that treatment with 500-800 ppm HOCl+Laponite does not significantly reduce or delay germination. (Estimated <6% compared to dry seed control, but no different to laponite control). FIG. 3.

The following shows tomato Moneymaker seeds treatment with HOCl hydrogel/hydrosol composition.

Tomato Moneymaker seeds were treated with HOCl-hydrogel composition. Seed weight to volume ratio was 0.5 g seed/100 ml of HOCl hydrogel composition (ActiVita) or DI control. The seeds were treated for 1 hour. Seeds were allowed to air dry with hydrogel composition residual for 16-24 hours before setting up seeds in a germination chamber.

Germination was investigated in 4 replicates of 25 seeds each. Germination was counted when the root radical appears.

Figure 4A:
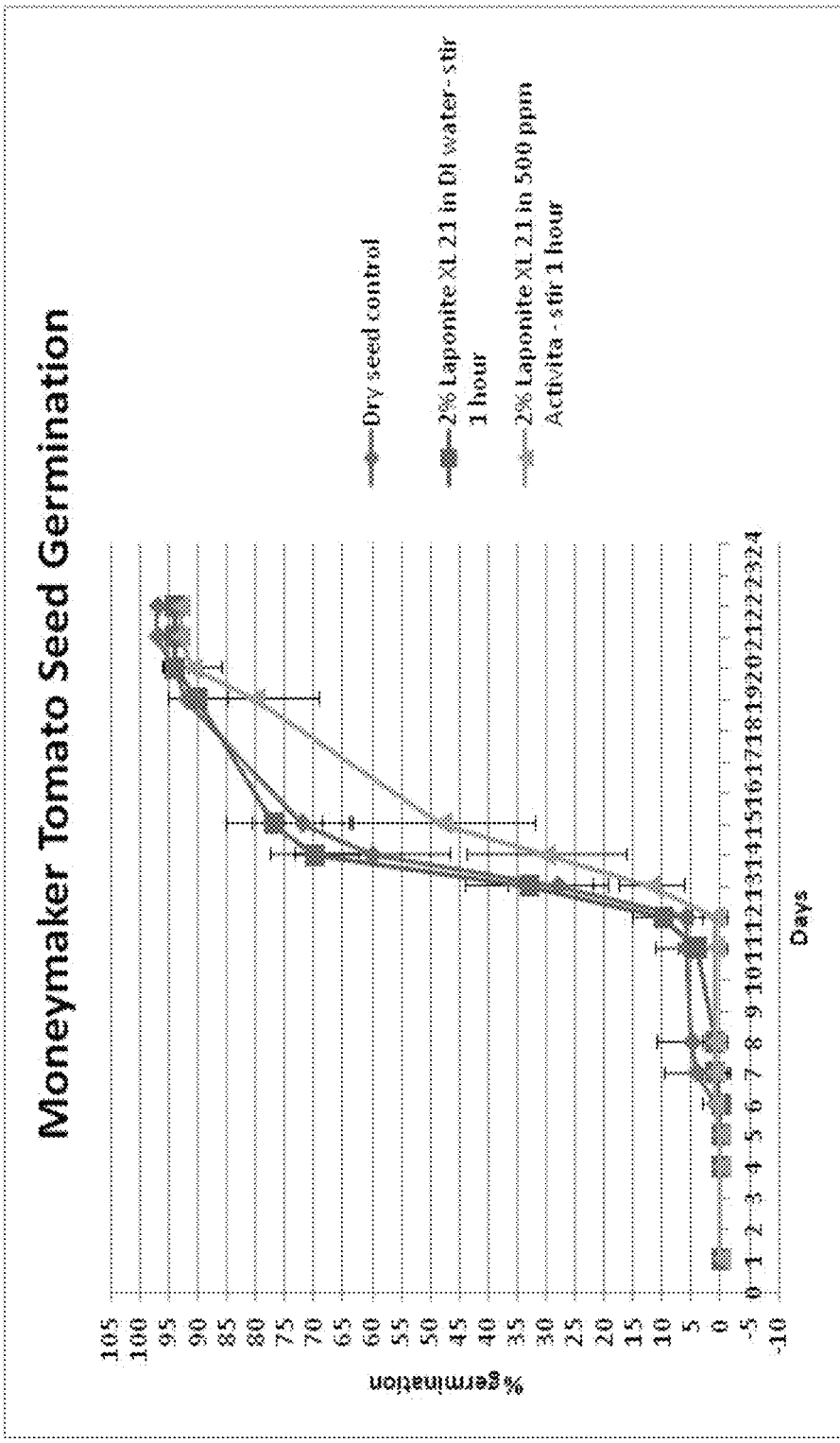
FIG. 4A shows percent germination over time.
Figure 4B:
FIG. 4B shows germination after pretreatment with the hypochlorous acid solution.

2% laponite with HOCl formulation only appears to slightly delay germination and does not significantly affect the final germination percentage (<5%). FIG. 4.

All references, issued patents and patent applications cited within the body of the instant specification are hereby incorporated by reference in their entirety, and for all purposes.

The invention claimed is:

1. A nutrient composition suitable for treatment of plants, seeds, or crops, comprising:
    an electrolyzed solution generated by electrochemical treatment of a 0.2 g/L to 200 g/L solution of potassium chloride (KCl), the electrolyzed solution comprising: oxidants content of from about 5 ppm to about 10,000 ppm, the oxidants comprising hypochlorous acid, dichlorine monoxide, oxygen, bicarbonate, and peroxicarbonate radicals; and a dissolved oxygen content of from 130% to 300% saturation; and
    a clay-based carrier producing a slurry or sol.

2. The composition of claim 1, further comprising potassium phosphate(s).

3. The composition of claim 1, wherein the electrolyzed solution is generated by electrochemical treatment of a 0.2 g/L to 10 g/L solution of potassium chloride (KCl).

4. The composition of claim 1, wherein the oxidants content is from about 20 to about 1,200 ppm.

5. The composition of claim 1, wherein the clay-based carrier is a kaolin clay, laponite clay, or silica-based clay material.

6. The composition of claim 1, wherein the composition comprises from about 0.5% to about 50% by weight of the clay-based carrier.

7. The composition of claim 6, wherein the composition comprises from about 0.5% to about 2% by weight of the clay-based carrier.

8. The composition of claim 1, wherein the pH of the electrolyzed solution is from about 3.5 to about 9.0.

9. The composition of claim 8, wherein the pH of the electrolyzed solution is from about 4.0 to about 8.0.

10. The composition of claim 1, wherein the composition is packaged for storage or sale in plastic or glass bottles or bags.

* * * * *